(12) United States Patent
McInnes

(10) Patent No.: US 6,322,577 B1
(45) Date of Patent: Nov. 27, 2001

(54) READILY EXCHANGEABLE PERFUSION DILATION CATHETER

(76) Inventor: Peter R. McInnes, 4 Grosvenor Court, Hawley Hill Camberley, Surrey (GB), GU179 JL (*) Notice: Subject to any disclaimer, the term of this patent is extended or adjusted under 35 U.S.C. 154(b) by 0 days.

(21) Appl. No.: 08/484,267

(22) Filed: Jun. 7, 1995

Related U.S. Application Data

(63) Continuation of application No. 08/183,574, filed on Jan. 18, 1994, now Pat. No. 5,516,336, which is a continuation of application No. 07/888,253, filed on May 22, 1992, now abandoned, which is a continuation of application No. 07/541,264, filed on Jun. 20, 1990, now abandoned, which is a continuation-in-part of application No. 07/476,056, filed on Feb. 7, 1990, now abandoned.

(51) Int. Cl.[7] .................................................. A61M 25/10
(52) U.S. Cl. ............................................. 606/194; 604/96
(58) Field of Search ..................................... 606/192–194; 604/96, 101, 102

(56) References Cited

U.S. PATENT DOCUMENTS

| | | | |
|---|---|---|---|
| 4,195,637 | 4/1980 | Gruntzig et al. | 128/348 |
| 4,413,989 | 11/1983 | Schjeldahl et al. | 604/96 |
| 4,423,725 | 1/1984 | Baran et al. | 128/207.15 |
| 4,545,390 | 10/1985 | Leary | 606/192 |
| 4,581,017 | 4/1986 | Sahota . | |
| 4,661,094 | 4/1987 | Simpson | 604/53 |
| 4,748,982 | 6/1988 | Horzewski et al. | 606/192 |
| 4,762,129 | 8/1988 | Bonzel | 604/96 |
| 4,771,777 | 9/1988 | Horzewski et al. | 606/194 |
| 4,820,349 | 4/1989 | Saab | 606/194 |
| 4,877,031 | 10/1989 | Conway et al. | 606/194 |
| 4,892,519 | 1/1990 | Songer et al. | 606/194 |
| 4,944,745 | 7/1990 | Sogard et al. | 606/194 |
| 4,988,356 | 1/1991 | Crittenden et al. | 606/194 |
| 5,002,531 | 3/1991 | Bonzel | 604/96 |
| 5,040,548 | 8/1991 | Yock . | |
| 5,046,503 | 9/1991 | Schneiderman | 606/194 |
| 5,061,273 | 10/1991 | Yock . | |
| 5,300,085 | 4/1994 | Yock | 606/191 |

OTHER PUBLICATIONS

L. Finci, et al., "Advances In Coronary Angioplasty", Cardio, Sep. 1987, pp. 53–57.

P. deFeyter, et al., "Short Term Results of Percutaneous Transluminal Coronary Angioplasty with the Monorauil Technique: Experience in the First 1000 Patients", Br. Heart J. 1990; 63:253–259.

Mar. 1986 abstract of the presentation of seminar in Europe. Nordenstrom articles published in 1962 and 1965 which describe a short guidewire receiving inner lumen in the distal end of an intravascular catheter.

*Primary Examiner*—Michael H. Thaler

(57) ABSTRACT

A perfusion-type dilatation catheter which can be rapidly exchanged for another catheter without the need for exchange wires or guidewire extension wires. The dilatation catheter has an elongated catheter body with a distal guidewire port in the distal end of the catheter and a proximal guidewire port at least 10 cm but not more than 50 cm from the distal port. The catheter body has a first inflation lumen which extends from the proximal end of the catheter body to the interior of a dilatation balloon adjacent the distal end of the catheter body. A second, much shorter inner lumen is disposed between the proximal and distal guidewire ports and is adapted to slidably receive a guidewire. A plurality of perfusion ports are provided both proximal and distal to the balloon which are in fluid communication with the second inner lumen so that when the balloon is inflated within a patient's vascular system, blood will flow through the proximal perfusion ports and the second inner lumen and out the distal perfusion ports to minimize ischemic conditions distal to the catheter. A stiffening member is disposed within the catheter body proximal to the proximal guidewire port to provide improved pushability. The distal portion of the inflation lumen should have a transverse cross-sectional area of about 3 to about $20 \times 10^{-5}$ $inch^2$ and should not be greater than one-third the cross-sectional area of the perfusion lumen.

12 Claims, 3 Drawing Sheets

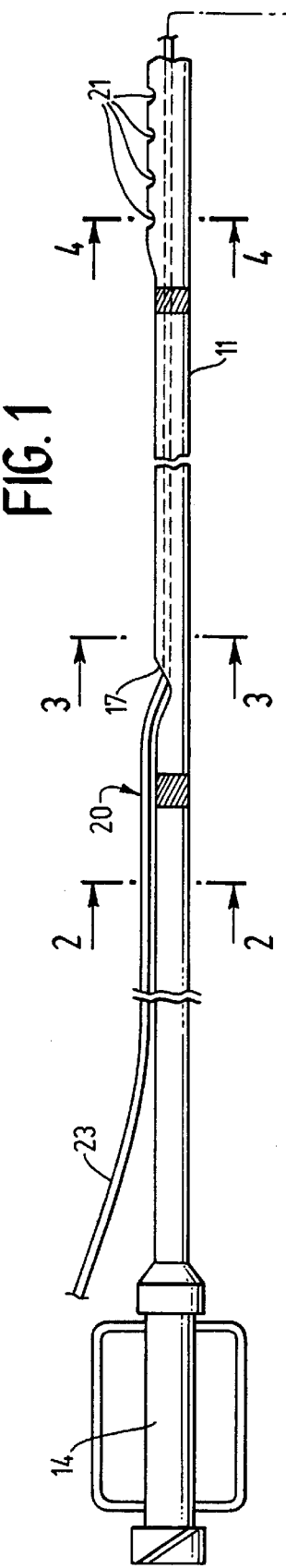
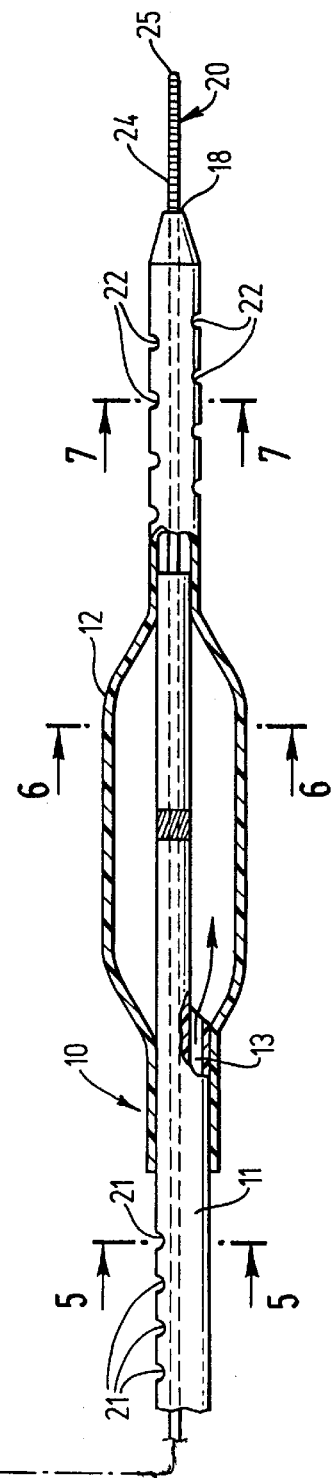
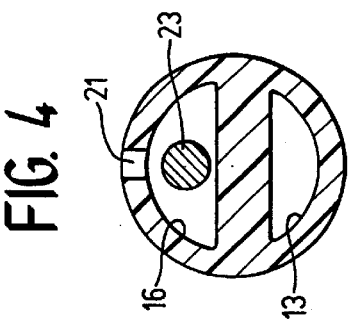
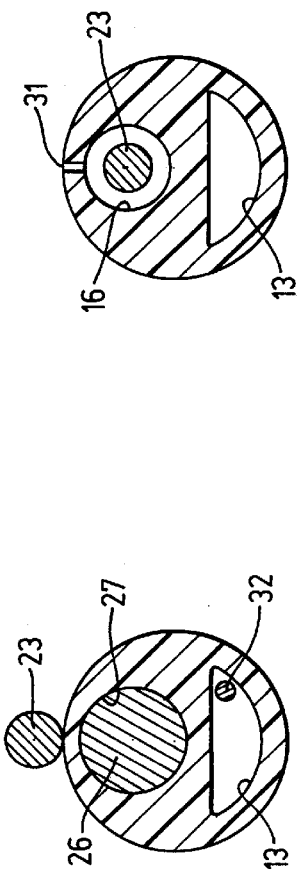
FIG. 1
FIG. 2
FIG. 3
FIG. 4

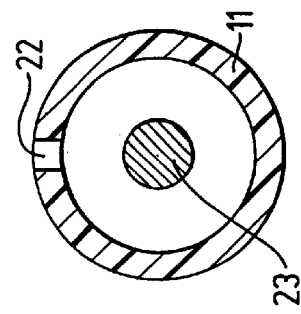
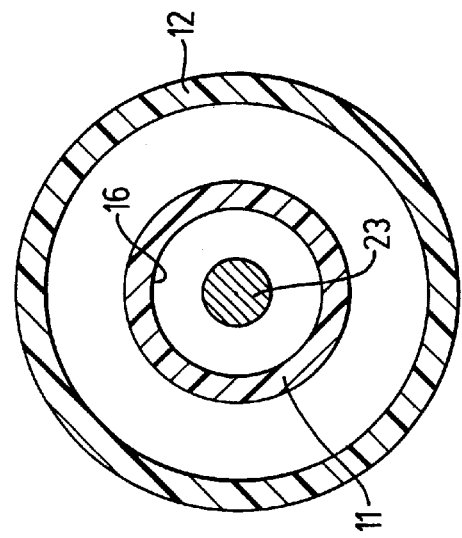
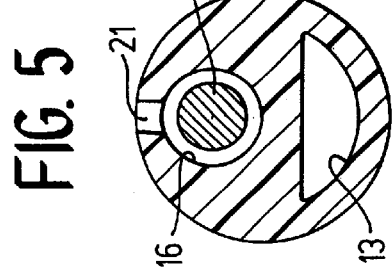
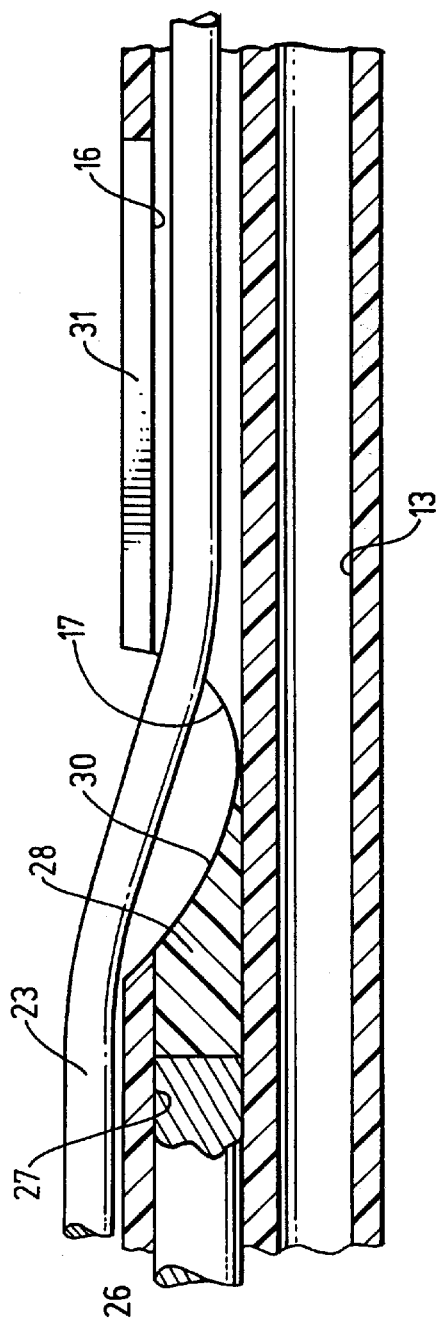

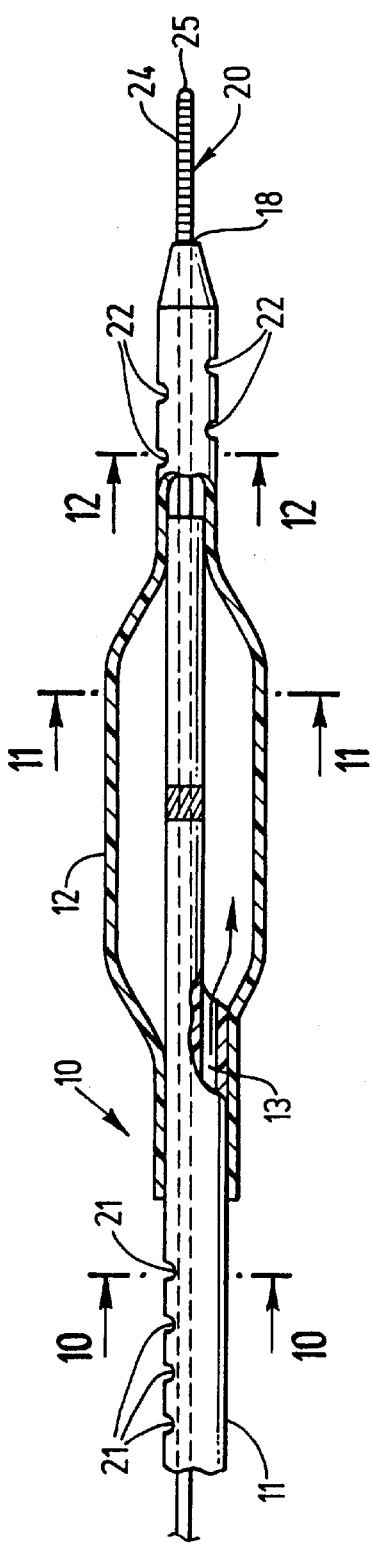
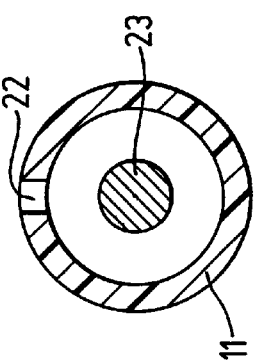
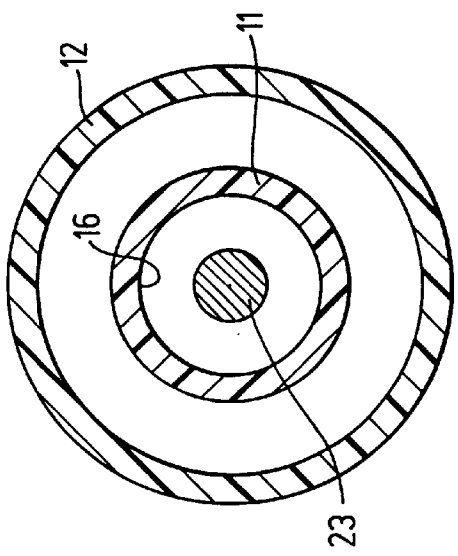
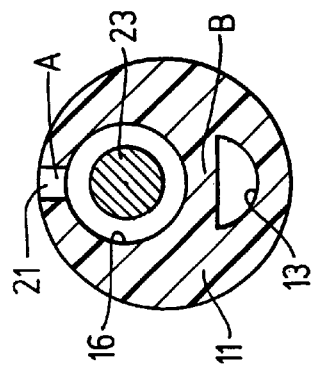

READILY EXCHANGEABLE PERFUSION DILATION CATHETER

This is a continuation application of application Ser. No. 08/183,574 which was filed on Jan. 18, 1994, now U.S. Pat. No. 5,516,336, which is a continuation of Ser. No. 07/888,253 filed May 22, 1992, now abandoned, which is a continuation of Ser. No. 07/541,264 filed Jun. 20, 1990, now abandoned, which is a continuation-in-part of Ser. No. 07/476,056 filed Feb. 7, 1990 now abandoned.

BACKGROUND OF THE INVENTION

This invention generally relates to a dilatation catheter for angioplasty procedures such as percutaneous transluminal coronary angioplasty (PTCA).

In PTCA procedures, a dilatation catheter having an inflatable, relatively inelastic balloon on the distal end thereof is advanced through a patient's arterial system until the balloon crosses the atherosclerotic lesion to be dilated. The balloon is inflated to a predetermined size with radiopaque liquid at relatively high pressures (e.g., 8 atmospheres) to dilate the stenotic region and then the balloon is deflated so that the catheter can be removed and blood flow resumed.

Usually a guiding catheter having a preformed distal end is first percutaneously introduced into the patient's arterial system and advanced therein until the distal tip of the guiding catheter is disposed in the appropriate ostium of the patient's coronary artery. A guidewire is preloaded within a dilatation catheter and both are advanced through the previously positioned guiding catheter to the distal end thereof. The guidewire is first advanced out of the guiding catheter into the patient's coronary anatomy until the distal end of the guidewire crosses the stenotic region to be dilated. The dilatation catheter is then advanced over the guidewire, with the guidewire slidably disposed within an inner lumen of the catheter until the inflatable balloon is positioned within the stenosis. The balloon is inflated to a relatively high pressure to dilate the stenosis and then deflated and removed over the guidewire. For a detailed description of procedures, reference is made to U.S. Pat. No. 4,332,254 (Lundquist), U.S. Pat. No. 4,323,071 (Simpson-Robert), U.S. Pat. No. 4,439,185 (Lundquist), U.S. Pat. No. 4,468,224 (Enzmann et al.), U.S. Pat No. 4,516,972 (Samson), U.S. Pat. No. 4,538,622 (Samson et al.), U.S. Pat. No. 4,554,929 (Samson et al.), U.S. Pat. No. 4,569,347 (Frisbie), U.S. Pat. No. 4,571,240 (Samson et al.), U.S. Pat. No. 4,638,805 (Powell), U.S. Pat. No. 4,748,982 (Horzewski et al.), all of which are hereby incorporated herein in their entirety by reference thereto.

Efforts have been made to develop dilatation catheters which perfuse blood through an inner lumen of the catheter which traverses the interior of the balloon when the balloon is inflated during angioplasty procedures in order to avoid ischemic conditions distal to the inflated balloon. For example, dilatation catheters providing perfusion capabilities are described in U.S. Pat. No. 4,423,725 (Baran et al.) and U.S. Pat. No. 4,790,315 (Mueller, Jr. et al.) which are incorporated herein by reference thereto. See also, U.S. Pat. No. 4,581,017 (Sahota). However, these perfusion dilatation catheters generally have relatively large deflated profiles and as a result they frequently are not employed in those situations where the stenoses to be treated are deep within the patient's coronary anatomy.

Additionally, in instances where there is an acute or sudden blockage of the arterial passageway after dilatation of a stenotic region, conventional dilatation non-perfusion type catheters must first be removed from the patient before a perfusion-type dilatation catheter can be advanced over the guidewire in place within the patient. Usually, such catheter exchanges require the use of an exchange wire or extension wire such as described in U.S. Pat. No. 4,827,941 (Taylor et al.), which can add considerable time and complexity to a procedure frequently performed under emergency conditions.

What has been needed and heretofore unavailable is a perfusion-type dilatation catheter which can quickly and easily be introduced into a patient's arterial system and which has sufficient pushability to be advanced deep within the patient's vasculature. The present invention satisfies this need.

SUMMARY OF THE INVENTION

The present invention is directed to a dilatation catheter which can be readily exchanged without the need for extension wires or for the replacement of the guidewire with an exchange wire and which can also perfuse blood distal to the catheter when a vascular procedure is being performed within the blood vessel which otherwise blocks the flow of blood through.

A catheter in accordance with the invention generally has an elongated catheter body with an inflatable, relatively inelastic balloon near the distal end thereof. The catheter body has a first elongated inner lumen extending from the proximal end of the catheter body to the interior of the inflated balloon near the distal end thereof to deliver inflation fluid to the interior of the balloon. A second, much shorter inner lumen extends within the distal portion of the catheter body between a proximal guidewire port and a distal guidewire port provided in the distal end of the catheter body. The distal guidewire port is in the very distal tip of the catheter body and the proximal guidewire port is at least 10 cm but not more than about 50 cm from the distal guidewire port. The second, much shorter lumen within the catheter body is adapted to slidably receive a guidewire to facilitate the advancement of the catheter over the guidewire into the patient's coronary anatomy.

At least one proximal perfusion port is provided in the catheter body between the proximal guidewire port and the proximal end of the balloon and at least one distal perfusion port is provided in the catheter body between the distal end of the balloon and the distal end of the catheter body. Both the proximal and distal perfusion ports are in fluid communication with the second, shorter lumen disposed within the catheter body so that blood flows distal to the catheter when the balloon is inflated during the vascular procedure. The number, size and location of the perfusion ports can be varied depending upon the blood flow required, the size of the catheter and the size of the inner lumen. Typically, there may be 6 to 20 perfusion ports proximal to the balloon and about 4 to 12 perfusion ports distal to the balloon. In a preferred embodiment 10 ports are provided proximal to the balloon and 4 are provided distal to the balloon.

The cross-sectional area of the last or most distal part of the inflation lumen, which is less than 30 cm, preferrably in the last 10 cm the inflation lumen proximal to the balloon, is at least about 3 to about $20 \times 10^{-5}$ inch$^2$ and should not be greater than about one-third of the cross-sectional area of the perfusion lumen. This reduces considerably the catheter profile, allowing the catheter to be advanced much deeper into a patient's coronary vasculature, yet maintains adequate inflation and deflation times (e.g. less that about 30 seconds preferrably less than about 20 seconds). The proximal end of the catheter body is provided with an adapter with at least one arm for the delivery of inflation fluid from a high pressure source thereof such as a syringe to the proximal end of the inflation lumen leading to the interior of the balloon for inflation purposes.

Preferably, the catheter wall which defines at least in part the second, shorter, guidewire-receiving lumen disposed within the catheter body is provided with a slit which extends from the proximal guidewire port to a location proximal to the section containing the proximal perfusion ports. The purpose of this slit, as described in U.S. Pat. No. 4,748,982 (Horzewski et al.) which has been previously incorporated herein, allows the guidewire to be pulled out of a significant portion of the second lumen to increase the ease in which catheters can be exchanged.

The portion of the elongated catheter body proximal to the proximal guidewire port is provided with a stiffening member such as a rod or wire which increases the pushability of the catheter and thereby allows for more distal advancement of the catheter into the patient's coronary anatomy than previous perfusion-type catheters.

In the performance of an angioplasty procedure utilizing the catheter assembly of the invention, it is preferred to preload the guidewire within the second shorter lumen of the catheter with the distal tip of the guidewire extending out of the distal tip of the catheter, and then advance the combined assembly through a guiding catheter previously disposed within the patient's vasculature with the distal tip of the guiding catheter disposed with the ostium of the patient's coronary artery. The guidewire is first extended out of the distal end of the guiding catheter into the patient's coronary artery until the distal tip of the guidewire crosses the stenotic region to be dilated. The dilatation catheter is then advanced out of the guiding catheter over the guidewire until the balloon on the dilatation catheter is positioned across the stenosis. The balloon is then inflated with the radiopaque liquid as conventionally practiced to dilate the stenosis.

An alternate procedure which has been found suitable comprises first advancing the guidewire through the guiding catheter and into the desired location within the patient's coronary anatomy and then mounting the dilatation catheter of the invention on the proximal end of the guidewire and advancing the catheter over the wire to the desired location within the patient's coronary arteries.

When the balloon is inflated, it occludes the artery and blocks normal blood flow therethrough. However, blood flows through the proximal perfusion ports, through the shorter second lumen, and then out the distal perfusion ports and the distal guidewire port located in the catheter body distal to the balloon. To maximize blood flow through the second lumen, it is preferred to withdraw the guidewire sufficiently from the dilatation catheter so that the distal portion of the guidewire remains in the second lumen but proximal to the portion of the second lumen between the proximal and distal perfusion ports. When the dilatation has been completed, the guidewire can then be advanced back through the second lumen and out the distal end thereof so that it crosses the stenosis.

In the event of an abrupt reclosure when the dilatation catheter is deflated, such as from a dissected lining, the balloon can be inflated in the stenotic region so as to maintain the patency of the artery. The artery may then be held open while blood perfuses therethrough for a long enough period to allow the dissected lining to be resecured to the blood vessel wall by natural healing or to allow for surgical procedures to be initiated to correct the abrupt reclosure, such as bypass surgery.

Should the catheter in place need to be replaced with another catheter, for example when the inflated diameter of the balloon on the catheter in place is too small to completely dilate a stenosis, a second catheter should then be inserted to complete the dilation. In this instance, the catheter of the invention can be readily replaced by holding onto the guidewire extending out the proximal end of the guiding catheter and pulling on the dilatation catheter to remove it from the patient. A second dilatation catheter of essentially the same construction but with a larger diameter balloon may then be mounted on the proximal end of the guidewire and then advanced over the guidewire into the stenosis for further dilation.

A similar situation arises when a second stenosis distal to the first stenosis needs to be dilated and the balloon on the catheter used to dilate the first stenosis is too large for the distal region. The same procedures may be followed to advance a catheter having a smaller balloon to the more distal stenosis.

The dilatation catheter in accordance with the present invention can be advanced deeply within the patient's vascular system, much further than prior perfusion catheters due to the increased pushability of the catheter. Thus, the catheter of the present invention allows for the long-term dilatation of stenoses which the prior perfusion catheters were unable to reach. Additionally, when a catheter in accordance with the present invention needs to be replaced with another catheter, such catheter exchanges can be quickly and very easily performed without the need for exchange wires or extension wires required with the prior art dilatation catheters. These and other advantages of the present invention will become more apparent from the following detailed description thereof when taken in conjunction with the attached exemplary drawings.

BRIEF DESCRIPTION OF THE DRAWINGS

FIG. 1 is an elevational view partially in section of a dilatation catheter embodying features of the invention;

FIG. 2 is a transverse cross-sectional view taken along the lines 2—2 shown in FIG. 1;

FIG. 3 is a transverse cross-sectional view taken along the lines 3—3 shown in FIG. 1;

FIG. 4 is a transverse cross-sectional view taken along the lines 4—4 shown in FIG. 1;

FIG. 5 is a transverse cross-sectional view taken along the lines 5—5 shown in FIG. 1;

FIG. 6 is a transverse cross-sectional view taken along the lines 6—6 shown in FIG. 1;

FIG. 7 is a transverse cross-sectional view taken along the lines 7—7 shown in FIG. 1;

FIG. 8 is a longitudinal, center line, cross-sectional view taken through the transition region of the catheter shown in FIG. 1 illustrating the extension of the guidewire through a proximal guidewire port and into an inner lumen of the dilatation catheter;

FIG. 9 is a partial elevational view, partially in section of an alternative dilatation catheter embodying features of the invention;

FIG. 10 is a cross-sectional view taken along the lines 10—10 shown in FIG. 9;

FIG. 11 is a cross-sectional view taken along the lines 11—11 shown in FIG. 9; and FIG. 12 is a cross-sectional view taken along the lines 12—12 shown in FIG. 9.

DETAILED DESCRIPTION OF THE INVENTION

The present invention is directed to a vascular catheter 10 having a elongated catheter body 11 with an inflatable balloon 12 near the distal end thereof. A first inner lumen 13 extends through a substantial portion of the catheter body 11 and is in fluid communication with the interior of the balloon 12. An adapter 14 is provided at the proximal end of the catheter body 11 which is in fluid communication with the first inner lumen 13 to direct inflation fluid from a high pressure source such as a syringe pump (not shown) to the interior of balloon 12.

A second lumen 16 is provided in a distal portion of the catheter 10 which remains within the patient during angioplasty or other vascular procedures. The second lumen 16 is much shorter than the first lumen and extends between a proximal guidewire port 17 and a distal guidewire port 18 which is located at the distal tip of the catheter body. The proximal guidewire port 17 is located about 10 to about 50 cm, preferably about 12 to about 40 cm, from the distal guidewire port 18. During the angioplasty procedures, the guidewire 20 is slidably disposed within the second inner lumen 16.

Proximal perfusion ports 21 are provided in the catheter body 11 between the proximal end of the balloon 12 and the proximal guidewire port 17 and distal perfusion ports 22 are provided between the distal end of the balloon and the distal end of the catheter body 11. Perfusion ports 21 and 22 pass through the wall of the catheter body 11 which defines at least in part the second inner lumen 16 and therefore are in fluid communication therewith.

The guidewire 20 generally includes a core member 23 and a flexible body such as a helical coil 24 on the distal portion of the core member. A rounded plug 25 is provided at the distal tip of the core to prevent traumatic engagement with the arterial lining. During angioplasty or other vascular procedures, the proximal guidewire port 17 remains within the guiding catheter, and the core member 23 of the guidewire 20 extends out of the proximal guidewire port and runs generally parallel to the catheter body within the guiding catheter (not shown).

Stiffening rod 26 is disposed within a third lumen 27 provided in the catheter body 11 proximal to the proximal guidewire port 17 and generally extends to the proximal end of the catheter body 11. For ease of manufacturing, the third lumen 27 and the second inner lumen 16 are essentially the same lumen with a plug 28 provided therein proximally adjacent the proximal guidewire port 17. Preferably the distal portion of the plug 28 is in the form of a ramp 30 which can guide the guidewire 20 into or out of the second inner lumen 16. The wall of the catheter body 11 defining the inner lumen 16 is provided with a slit 31 from the proximal guidewire port 17 to a location proximal to the proximal perfusion port 21 through port 17.

The first inner lumen 13 is preferably provided with a small diameter wire member 32 which prevents the retention of air bubbles at the corners of the D-shaped first lumen. The wire member 31 preferably does not extend along essentially the entire length of the inflation lumen 13.

The various components of the catheter of the present invention can be made from conventional materials. Catheter body 11 can be extruded or otherwise formed from plastic resins such as polyethylene and polyesters (e.g., Hytrel) and the balloon can be formed from polyethylene or polyethylene terephthalate resins. The core 23 of the guidewire 20 can be made of stainless steel and the coil 24 can be made of a more highly radiopaque material such as platinum, tungsten, palladium, ruthenium, rhenium and alloys thereof. A wide variety of other suitable materials can also be used for these components.

For coronary angioplasty procedures, the outer diameter of the catheter body 11 proximal to the perfusion section can typically range from about 0.035 to about 0.05 inch (0.89–1.30 mm.) and the perfusion section thereof can range from about 0.04 to 0.06 inch (1.02–1.52 mm.). Inflatable balloon diameters can range from about 1.5 to about 4.5 mm. The stiffening element is a rod or wire preferably with a circular transverse cross-section ranging in diameter from about 0.015 to about 0.025 inch (0.38–0.64 mm.). The diameter of the guidewire lumen 16 in the perfusion section of the catheter body 11 may vary from about 0.02 to about 0.045 inch (0.51–1.14 mm.), but the opening in the distal tip of the catheter may range from about 0.015 to about 0.025 inch (0.38–0.64 mm). The overall length of the catheter body 11 from the distal tip to the adapter 14 may be about 130 to about 150 cm. The aforesaid dimensions are believed to be suitable for most coronary angioplasty procedures. Angioplasty procedures at other locations and catheters for other procedures (e.g., atherectomy procedures) may require dimensions different than those described above.

FIGS. 8–12 illustrate an alternate embodiment which provides a rapid exchange dilatation catheter with perfusion characteristics with an improved low profile distal portion. The proximal portion of the catheter and the balloon 12 and portions distal thereto are essentially the same as that shown in FIGS. 1–7. The improvements of the embodiment shown in FIGS. 8–11 involve the distal portion of the catheter between the proximal guidewire port 17 and the balloon 12 wherein the ratio of the cross sectional area of the inflation lumen 13 to the cross-sectional area of the perfusion lumen 16 is controlled so that the former lumen is not greater than about one-third of the latter. Preferably, the inflation lumen 13 is D-shaped or crescent-shaped along its entire length, whereas the perfusion lumen 16 is essentially circular along its length. A proximal portion of the perfusion lumen, e.g., the first 24 cm may however, be shaped to reduce the profile in this section as shown in FIG. 4. Additionally, the inflation lumen should have a cross-sectional area of about 3 to about $20 \times 10^{-5}$ inch$^2$. However, in order to maintain reasonable inflation and deflation times (e.g. less than about 30 seconds, preferably less than about 20 seconds) the length of the inflation lumen having the aforesaid cross-section should not exceed 20 cm. The inflation lumen in the catheter body 11 leading to the portion having the smaller transverse dimensions is typically about $65 \times 10^{-5}$ inch$^2$. The details for the guidewire lumen and the perfusion lumen are described with the embodiment shown in FIGS. 1–7. Typical dimensions for the cross-section shown in FIG. 9 include a height of about 0.007 inch and a base of about 0.026 inch for the inflation lumen, a radius of about of 0.019 inch for the perfusion lumen, a wall thickness of about 0.005 inch at location A between the perfusion lumen and the exterior of the catheter body 11 and a wall thickness of about 0.006 inch at location B between the perfusion lumen and the inflation lumen. The outer diameter of the catheter body is about 0.052 inch, which is to be compared to an outer diameter of about 0.057 inch for the embodiment shown in FIGS. 1–7.

The catheter of this embodiment has great pushability and perfusion of blood to the distal portion of the coronary artery. The lower profile and enhanced pushability allows the catheter to be advanced much farther into a patient's coronary anatomy than prior perfusion catheters.

While the present invention has been described herein in terms of certain specifically preferred embodiments specifically directed to coronary angioplasty procedures, various modifications and improvements can be made without departing from the scope of the invention.

What is claimed is:

1. A dilation catheter for rapid movement over a guidewire into a desired location within a patient's artery which perfuses oxygenated blood distal to the catheter, comprising:
   a) an elongated catheter body having proximal and distal ends, a distal guidewire port in the distal end, a proximal guidewire port spaced at least 12 cm from the distal end and a substantial distance from the proximal end, a proximal shaft section and a distal shaft section which is substantially shorter and more flexible than the proximal shaft section;
   b) an extensible dilation member which is located on the distal shaft section proximal to the distal end thereof and distal to the proximal guidewire port and which has an interior suitable for receiving inflation media;
   c) a guidewire receiving lumen configured to slidably receive a guidewire which extend between the distal guidewire port and the proximal guidewire port and which is in fluid communication therewith;
   d) an inflation lumen which extends from the proximal end of the catheter body to a location spaced from the distal end of the catheter body and which is in fluid communication with the interior of the extensible dilation member;
   e) the distal shaft section having a perfusion portion proximal to the extensible dilation member and a non perfusion portion proximal to the perfusion portion and distal to the proximal guidewire port, the perfusion portion having an outer maximum transverse dimension much larger than the outer maximum transverse dimension of the non-perfusion portion;
   f) a plurality of proximal perfusion ports which extend along a length of the perfusion portion of the distal shaft section and which are in fluid communication therewith.

2. The dilatation catheter of claim 1 wherein the proximal guidewire port is spaced about 12 to about 40 cm from the distal end of the catheter.

3. The dilatation catheter of claim 1 wherein the extensible dilatation member is a balloon which has proximal and distal skirts and which is secured by said skirts to the distal shaft section proximally adjacent the distal end of the catheter body and distal to said perfusion portion of the distal shaft section.

4. The dilatation catheter of claim 3 wherein the dilation balloon is formed of a relatively inelastic material.

5. The dilatation catheter of claim 1 including means to stiffen the proximal shaft section.

6. The dilatation catheter of claim 4 wherein the means to stiffen the proximal shaft section is a mandrel.

7. The dilation catheter of claim 1 wherein a slit is provided in the non-perfusion portion of the distal shaft section which extends from the proximal guidewire port to a location proximal to the perfusion portion of the distal shaft section.

8. The dilatation catheter of claim 1 wherein the perfusion portion of the distal shaft section is provided with about 6 to about 20 perfusion ports.

9. The dilatation catheter of claim 8 wherein the perfusion portion of the distal shaft section is about 0.04 to about 0.06 inch in maximum transverse dimension.

10. The dilation catheter of claim 8 wherein the non-perfusion portion of the distal shaft section is about 0.035 to about 0.05 inch in maximum transverse dimension.

11. The dilatation catheter of claim 1 wherein the distal shaft section is provided with about 4 to about 12 perfusion ports distal to the extensible dilation member.

12. The dilatation catheter of claim 1 wherein the guidewire lumen extending through the perfusion portion of the distal shaft section has a transverse cross-sectional area and the inflation lumen extending through the perfusion portion of the distal shaft section has a transverse cross-sectional area which is not greater than one-third of the transverse cross-sectional area of the guidewire lumen extending through the perfusion portion of the distal shaft section.

* * * * *

UNITED STATES PATENT AND TRADEMARK OFFICE
CERTIFICATE OF CORRECTION

PATENT NO. : 6,322,577 B1 Page 1 of 1
DATED : November 27, 2001
INVENTOR(S) : Peter McInnes et al.

It is certified that error appears in the above-identified patent and that said Letters Patent is hereby corrected as shown below:

<u>Title page,</u>
Item [76], Inventor: please correct Peter R. McInnes, 4 Grovesnor Court, Hawley Hill Camberley, Surrey (GB), GU179 JL" should be changed to -- [76] Inventors: Peter R. McInnes, Camberley, Surrey (GB); Motasim M. Sirhan, Sunnyvale, California (US) --.

Item [73], Assignee: insert -- Advanced Cardiovascular Systems, Inc., Santa Clara, CA (US)" --.

Signed and Sealed this

Twenty-third Day of July, 2002

*Attest:*

*Attesting Officer*

JAMES E. ROGAN
*Director of the United States Patent and Trademark Office*